United States Patent [19]

Cardenas et al.

[11] 4,205,187

[45] May 27, 1980

[54] PROCESS FOR PREPARING P,P'-BIPHENOL OF HIGH PURITY

[75] Inventors: Jorge N. Cardenas, Somerville; Walter T. Reichle, Warren, both of N.J.

[73] Assignee: Union Carbide Corporation, New York, N.Y.

[21] Appl. No.: 120

[22] Filed: Jan. 2, 1979

[51] Int. Cl.² ............................................. C07C 37/00
[52] U.S. Cl. ...................................... 568/730; 568/805
[58] Field of Search ............................... 568/730, 805

[56] References Cited

U.S. PATENT DOCUMENTS

| | | | |
|---|---|---|---|
| 2,792,427 | 5/1957 | Hoatson et al. | 260/613 |
| 3,091,646 | 5/1963 | Leston | 568/784 |
| 3,153,098 | 10/1964 | Boag | 260/620 |
| 3,284,514 | 11/1966 | Dedmas et al. | 568/805 |
| 3,562,338 | 2/1971 | Zaweski | 568/730 |
| 3,575,815 | 4/1971 | Sech | 202/176 |
| 3,631,208 | 12/1971 | Itay | 260/619 R |
| 3,813,445 | 5/1974 | Masne | 260/620 |
| 4,085,124 | 4/1978 | Rutledge | 260/396 N |
| 4,086,253 | 4/1978 | Hopper et al. | 260/396 N |
| 4,093,598 | 6/1978 | Banucci et al. | 260/47 ET |
| 4,096,190 | 6/1978 | Rutledge | 568/730 |
| 4,098,766 | 7/1978 | Rutledge | 528/217 |
| 4,098,830 | 7/1978 | Rutledge | 568/730 |
| 4,100,202 | 7/1978 | Rutledge | 568/730 |
| 4,100,203 | 7/1978 | Rutledge | 568/730 |
| 4,100,204 | 7/1978 | Rutledge | 568/730 |
| 4,100,205 | 7/1978 | Rutledge | 568/730 |
| 4,100,206 | 7/1978 | Rutledge | 568/730 |
| 4,101,561 | 7/1978 | Rutledge | 568/730 |

FOREIGN PATENT DOCUMENTS

| | | | |
|---|---|---|---|
| 6514147 | 5/1967 | Netherlands | 568/805 |
| 1118287 | 6/1968 | United Kingdom | 568/805 |

OTHER PUBLICATIONS

Jones et al., "Ind. Eng. Chem.", vol. 44, No. 12, pp. 2872–2876 (1952).

Jones et al., "Ind. Eng. Chem.", vol. 45, No. 12, pp. 2704–2705 (1953).

*Primary Examiner*—Norman Morgenstern
*Attorney, Agent, or Firm*—Donald M. Papuga

[57] ABSTRACT

A process for preparing p,p'-biphenol is provided which comprises heating a 4,4'-bis(substituted phenol) at elevated temperatures below the decomposition temperature of p,p'-biphenol in the absence of a catalyst under an inert, non-reactive atmosphere for the length of time sufficient to obtain a reaction product containing a substantial amount of p,p'-biphenol while, preferably, removing the olefin by-product formed and then recovering the p,p'-biphenol product.

5 Claims, No Drawings

PROCESS FOR PREPARING P,P'-BIPHENOL OF HIGH PURITY

The present invention relates to the preparation of biphenols and more particularly, to a process for preparing p,p'-biphenol (4,4'-dihydroxy biphenyl) of high purity and improved color by dealkylation of multi substituted biphenols.

Biphenols, and particularly substituted biphenols, have found wide utility as bacteriacides, chemical intermediates, copolymers, and antioxidants. For example, biphenols, especially those from 2,6-disubstituted phenols, are used to stabilize such materials as animal and vegetable fats or oils, gasoline, lubricants, rubber compositions, and the like. Moreover, unsubstituted biphenol, such as p,p'-biphenol have been found of interest in the preparation of a variety of polymeric resins, e.g. polyester and polycarbonate resins, wherein the biphenol is used as the dihydroxyl compound which is reacted with phosgene or with dibasic acids, polyepoxides, polyurethanes etc. It can also be used to make completely aromatic resins which exhibit good physical and mechanical properties combined with superior oxidative and solvent resistance. In the past, however, biphenols have been rather difficult and costly to produce because of the involved procedures required, the tendency to produce undesirable by-products, and the difficulty in obtaining a product of the purity and color characteristics desired for resin use. As a result, biphenols have not found the wide use in the preparation of resins, such as polyesters and polycarbonates that might have been expected.

Heretofore, multisubstituted biphenols have been generally prepared by the oxidative dimerization of various substituted phenol reactants in the presence of metallic or high concentrations of strongly alkaline catalysts to form the corresponding diphenoquinones. The quinones are recovered and may then be reduced with a reducing agent, such as hydrogen or an excess of a substituted phenol, to the corresponding substituted biphenol.

In U.S. Pat. No. 3,562,338 to Zaweski, a process is disclosed which eliminates the need to separate intermediate reaction products formed during the oxidation of substituted phenols prior to the final reaction step, wherein the diphenoquinone is converted to the substituted biphenol, but the process still involves two process stages to produce the desired substituted biphenols. In this process, substituted phenols are reacted with an oxygen containing gas in the presence of high concentrations of an alkali metal hydroxide catalyst until substantially all the substituted phenol has been oxidized to the diphenoquinone. A second portion of substituted phenol is then added, and the reaction mixture is heated to a temperature of from about 100° C. to 350° C. in the substantial absence of oxygen and maintained there until a reaction product containing a substantial amount of substituted biphenol is formed.

Also recently disclosed, for example, in U.S. Pat. Nos. 4,085,124 and 4,096,190 to Rutledge, are processes for the oxidative coupling of alkyl phenols and the like to directly prepare dimers thereof, wherein the coupling reaction is carried out in an aqueous medium in the presence of various alkaline and/or amine or metal complex catalysts. While the processes are disclosed as directly preparing substituted biphenols in a generally one stage reaction, the products formed thereby contain a mixture of substituted biphenols, substituted diphenoquinones, and polymers from which the desired substituted biphenol must then be separated.

Preparation of p,p'-biphenol directly by the oxidative coupling reaction system is not possible, since phenol itself cannot be oxidized to the corresponding biphenol and/or diphenoquinone. To produce p,p'-biphenol itself, as for example disclosed in U.S. Pat. No. 2,368,361, it has been generally necessary to start with diphenyl, which is sulfonated to the corresponding p,p'-disulfonic acid followed by alkali fusion and then acidification to produce the biphenol. Such a process, however, produces large quantities of undesirable inorganic by-products and requires the use of expensive construction materials for the reactors.

It has also been suggested, as for example disclosed in the U.S. Pat. No. 3,631,208 to Hay, to prepare p,p'-biphenol by dealkylation of various substituted biphenols using conditions and catalyst known in the art for causing dealkylation. In such patent, however, there is shown dealkylation of certain 4,4'-bis(2,6-disubstituted phenols) at elevated temperatures only in the presence of aluminum isopropoxide or aluminum phenoxide catalysts while continuously distilling off isobutylene and/or other olefinic by-products. Moreover, the p,p'-biphenol produced by the dealkylation process is shown to be primarily recovered by generally known crystallization techniques.

A number of dealkylation methods for use with phenols having substituents other than the hydroxyl group nuclearly attached to the benzene ring are known in the art. In general, dealkylation of substituted phenols under thermal conditions in the presence of a variety of different catalyst systems is most widely used, the type of substituent or substituents and location thereof on the benzene ring and extent of dealkylation desired being determinative of the specific combination of temperature and catalyst employed. Further, these processes are generally carried out in the liquid state using a solvent, though vapor phase dealkylation is also known and used. In U.S. Pat. No. 3,091,646 to Leston, for example, it is pointed out that thermal dealkylation of di-tertiary alkyl phenols without the aid of a catalyst has been found to be inefficient and workers in the art have resorted to catalytic dealkylation. It is also disclosed by patentee that liquid phase dealkylation has been generally preferred.

While the use of a catalyst is generally believed to be essential for the efficient dealkylation of alkyl phenols, and a great number of catalysts are known, it would be preferable from a product purity and plant practice standpoint to carry out such dealkylation without the use of any catalyst, and, most advantageous, if the process could be carried out without the need for a solvent. Moreover, known techniques are, in general, used for dealkylation of substituted phenols having only one benzene ring and the applicability of such procedures for use with substituted biphenols or phenols having more than one benzene ring is not certain and would be subject to the need for further evaluation.

There is disclosed, for example in U.S. Pat. No. 2,792,427 to Hoatson et al. a process for the preparation of a particular mononuclear tertiary alkyl phenol using a selective partial thermal dealkylation technique in the absence of a catalyst. Patentees' process, however, deals solely with the partial thermal dealkylation of a selected type of mononuclear tertiary alkyl phenol and is directed to a sequential series of dealkylation steps wherein, through the use of suitable recycle arrangements of a mixture of reactants distilled off during the dealkylation stage, substantially complete conversion of a disubstituted mononuclear phenol to a monosubstituted phenol is achieved. Hoatson et al disclose, therefore, that thermal dealkylation of a selected disubstituted mononuclear phenol, in the absence of a catalyst, will produce products that contain a mixture of various substituted phenol components, and it is only through the use of a suitable recycle arrangement that the desired partial dealkylation can be achieved.

As pointed out hereinabove, development of a process that could be used to readily and economically produce p,p'-biphenol containing no substituents other than hydroxyl groups on the dinuclear phenol would be highly desirable. Especially advantageous would be a process that could be used for the preparation of 4,4'-biphenol having improved purity and color characteristics.

In accordance with the present invention there is provided a process for producing p,p'-biphenol which comprises heating a 4,4'-bis(substituted phenol) at an elevated temperature below the decomposition temperature of p,p'-biphenol in the absence of a catalyst under a non-reactive atmosphere for the time necessary to obtain a reaction product containing a substantial amount of p,p'-biphenol while, preferably, removing the olefin by-products formed, and then recovering said p,p'-biphenol product.

Preferably, the process is carried out for the time necessary to substantially dealkylate all of the substituent groups except the hydroxyl groups from the substituted biphenol reactant while continuously removing by-products such as isobutylene therefrom, and then recovering said p,p'-biphenol by evaporation and condensation.

Also provided in accordance with the invention is a process for preparing p,p'-biphenol which comprises:

(1) contacting a phenol having the formula

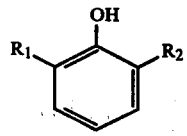

wherein $R_1$ and $R_2$ may be the same or different and is a member selected from the group consisting of alkyl radicals containing from 2 to 10 carbon atoms, aralkyl radicals containing from 8 to 10 carbon atoms and having a β alkyl carbon-hydrogen group, and cyclic alkyl radicals having a β alkyl carbon-hydrogen group with oxygen or an oxygen containing gas in the presence of a catalytic quantity of a catalyst selected from the group consisting of alkali metal hydroxides, alkali metal salts of a weak acid, alkaline earth metal hydroxides, alkaline earth metal salts of a weak acid, amine bases, and mixtures of the same at an elevated temperature, such as, for example, from about 50° C. to about 240° C., for the time necessary to react up to a stoichiometric, and preferably less than a stoichiometric amount of oxygen with said phenol to form a reaction product containing a substantial amount of 4,4'-bis(2,6-disubstituted phenol), (2) dealkylating the substituent groups other than hydroxyl from said biphenol to prepare a reaction product containing a substantial amount of p,p'-biphenol and then (3) recovering said p,p'-biphenol.

The oxidative dimerization reaction readily proceeds to prepare the the desired disubstituted biphenols while the reaction products are surprisingly and unexpectedly substantially free of diphenoquinones.

The dealkylation reaction is carried out after completion of the oxidation coupling reaction without any further processing of the substituted biphenol produced thereby or may be carried out after the biphenol is discharged from the oxidation reaction vessel and charged to a separate reaction vessel for dealkylation. Preferably, the dealkylation process employed comprises heating the 4,4'-bis(2,6 disubstituted phenol) at an elevated temperature below the decomposition temperature of p,p'-biphenol, such as from about 250° C. to about 500° C., in the absence of catalyst under an inert, non-reactive atmosphere while, preferably, continuously removing the olefin by-product formed, for the time necessary to obtain a reaction product containing a substantial amount of p,p'-biphenol. Recovering the p,p'-biphenol product is most advantageously by using an evaporation and condensing technique.

The 4,4'-bis(substituted phenol) which may be employed as starting materials are biphenols having the general formula:

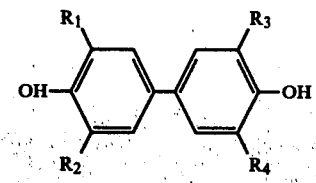

wherein $R_1$, $R_2$, $R_3$ and $R_4$ may be the same or different substituents selected from the group consisting of hydrogen, alkyl radicals containing from 2 to 10 carbon atoms, and aralkyl radicals containing from 8 to 10 carbon atoms and having a β alkyl carbon-hydrogen group with at least one of said R substituents being other than hydrogen. Typical substituted biphenols that may be employed are 3,3',5,5'-tetraethyl-4,4'-biphenol; 3,5-isopropyl-3'5'-diethyl-4,4'-biphenol; 3,3',5,5'-tetra-t-butyl-4,4'-biphenol; 3,3'-diethyl-4,4'-biphenol; 3,3'-diisopropyl-4,4'-biphenol; 3,3',5,5'-tetra sec. butyl-4,4'-biphenol; 3,3',5,5'-tetra-ethylphenyl-4,4'-biphenol.

Dealkylation of the substituted biphenol in accordance with the invention is conducted, for example, by charging a suitable substituted biphenol to a reaction vessel and then heating to a temperature below the decomposition temperature of p,p'-biphenol but high enough to effect dealkylation of the substituted biphenol. It is important for carrying out the dealkylation reaction and obtaining a p,p'-biphenol reaction product of high purity that the atmosphere in the reaction vessel contains substantially no oxygen or oxygen containing gas, and preferably, that the dealkylation reaction is carried out in an inert, non-reactive atmosphere. Carrying out the dealkylation reaction under a blanket of nitrogen or carbon dioxide gas is especially advantageous.

The dealkylation reaction of the invention is favored if the olefin by-product such as isobutylene is removed from the reaction vessel, and preferably, continuously expelled as formed during the course of the dealkylation reaction.

As pointed out hereinabove, the dealkylation reaction can be conducted over a wide temperature range below the decomposition temperature of p,p'-biphenol. In general, thermal dealkylation of suitable substituted biphenols can be carried out in the absence of a catalyst over a temperature range from about 250° C. to about 500° C., and preferably from about 290° C. to about 400° C.

The pressure at which the dealkylation reaction can be carried out is not narrowly critical and, in general, can be conducted under reduced pressures as low as about 200 mm Hg, or at higher pressures up to about 500 psig. A most useful pressure range is from about 1 to about 2 atmospheres gage pressure. To insure that an inert, non-reactive atmosphere is maintained in the reaction vessel, the atmosphere can be controlled by a flow of suitable gas into or through the reaction vessel. The removal of olefin by-product from the reaction vessel may also be achieved by controlled flow of inert gas through the reaction vessel or, alternatively, by periodic or continuous venting of the reaction vessel.

The use of a solvent for the substituted biphenol to be dealkylated or for the p,p'-biphenol reaction product is advantageously not required in accordance with the present invention. In general, the thermal dealkylation reaction in the absence of a catalyst is carried out at a temperature above the melting point of the substituted biphenol starting material, thereby permitting the dealkylation reaction to be carried out in the liquid state without the need for a solvent, and, advantageously, the need for elimination of solvents and catalysts from the desired reaction product is not required. Moreover, if desired, the olefin by-product of the dealkylation reaction may be recovered by conventional procedures.

The dealkylation reaction should be carried out for the time sufficient to convert substantially all of the substituted biphenol starting material to p,p'-biphenol. The length of time required to achieve substantially complete dealkylation of the substituted biphenol starting material will depend primarily upon the operating temperature and the type of substituted biphenol used as a starting material. In general, the rate of olefin by-product generation is also a factor in determining the operating temperature to be used, since the capability of removing the by-product generated at any particular operating temperature may limit the conditions used for carrying out the dealkylation reaction. For example, when using 2,2',6,6'-tetra-tert-butyl-4,4'-biphenol as a starting material, thermal dealkylation of the biphenol at a temperature of about 300° C. will result in a moderate rate of isobutylene formation and the dealkylation reaction time to achieve substantially complete dealkylation will be about 3 hours. Using a dealkylation reaction temperature of about 330° C., however, will generally result in a significantly greater rate of isobutylene generation and the dealkylation reaction cycle will be completed in about 2 hours.

Conducting the thermal dealkylation reaction of the present invention for the time necessary to achieve substantially complete dealkylation of substituted biphenol starting material, i.e., achieving at least about 95 percent conversion to p,p'-biphenol, is preferred since recovery by evaporation or distillation techniques of the desired p,p'-biphenol product from a reaction mixture containing substantial proportions of intermediate substituted biphenols having vapor pressures close to that of the desired unsubstituted biphenol is difficult.

Upon completion of the dealkylation reaction, the crude reaction product contains mostly p,p'-biphenol. However, the purity and color of the p,p'-biphenol reaction product is generally not suitable to enable it to be used directly as a polymerization monomer for forming polymers such as polyesters, polycarbonates and the like. Recovery of the p,p'-biphenol in the desired purity may be obtained by well-known techniques, such as by distillation, fractional crystallization, etc.

Recovering p,p'-biphenol with the purity (>99%) and color characteristics desired for use as a polymerization monomer by conventional crystallization techniques is complicated and requires a series of process steps. Distillation techniques are somewhat less complicated and therefore preferred. In accordance with the present invention, however, a particularly preferred method of removing p,p'-biphenol is by an evaporation and condensation procedure wherein the pressure in the reaction vessel containing the p,p'-biphenol reaction product is reduced to low pressures (to about 40 mm-Hg or lower) while maintaining the temperature at least about 290° C., and then recovering the p,p'-biphenol by precipitation out of the vapor phase by cooling the gas to about 50° C. and collecting the purified product in a separate receiver. A p,p'-biphenol product of greater than 99 percent purity and snow white color which is suitable for use directly as a polymerization monomer is thereby readily obtained in high yields.

While substituted biphenols that are suitable as starting materials for use in preparing p,p'-biphenol in accordance with the present invention may be prepared by a variety of procedures known in the art there is provided in accordance with the present invention an especially advantageous method for preparing p,p'-biphenol from various substituted phenols.

The phenols which may be employed as starting materials in the process of the invention are phenols having the general formula

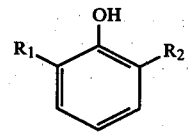

wherein $R_1$ and $R_2$ may be the same or different substituents selected from the group consisting of alkyl radicals containing from 2 to 10 carbon atoms, aralkyl radicals containing from 8 to 10 carbon atoms having a $\beta$ alkyl carbon-hydrogen group, and cyclic alkyl radicals having a $\beta$ alkyl carbon-hydrogen group. Preferably, $R_1$ and $R_2$ may be the same or different substituents selected from the group consisting of alkyl radicals containing 2 to 10 carbon atoms, and aralkyl radicals containing from 8 to 10 carbon atoms having a $\beta$ alkyl carbon-hydrogen group.

Typical phenols that may be employed are 2,6-di-sec-butyl phenol; 2,6-diisopropylphenol; 2-butyl-6-cyclohexylphenol; 2,6-ethyl phenol and preferably 2,6-di-tert-butylphenol.

In accordance with the process of the invention an essential component of the reaction mixture is a catalytic amount of a catalyst, suitable catalysts being selected from the group consisting of alkali metal hydroxides, alkali metal salts of a weak acid, alkaline earth metal hydroxides, alkaline earth metal salts of a weak acid, amine bases, and mixtures of the same. Illustrative of suitable catalysts are sodium hydroxide, potassnium hydroxide, barium hydroxide, rubidium hydroxide, cesium carbonate, rubidium carbonate, potassium sulfite, sodium borate, potassium acetate, pyridine, and 1,4-diazabicyclo-(2,2,2)-octane (DABCO).

The amount of catalyst used is not narrowly critical, but only a small amount is sufficient to promote dimerization of the phenols. In general, the amount used is as little as about 0.1 weight percent, though amounts up to about 1 weight percent are useful, and even greater amounts of catalyst may be used if desired.

In a preferred embodiment, at least a small amount of water or of a hydroxy containing lower alkyl compound such as ethyl or methyl alcohol is added to the reaction mixture. It has been found that the presence of amounts of at least 0.01 weight perecent of the reaction mixture of said additive may be sufficient to eliminate the induction period of the oxidative dimerization reaction but greater amounts may be used if desired.

In the practice of the invention, the amount of oxygen employed relative to the phenol is quite critical. In general, only an amount of oxygen up to that stoichiometrically required for the direct oxidative dimerization of a disubstituted phenol to the corresponding biphenol should be used, but it is preferred to use less than stoichiometrically required.

The reaction is conducted, for example, by passing oxygen, and preferably an oxygen containing gas such as air, through the reaction mixture in a reaction vessel with agitation to obtain intimate contact of the reactants. The reaction can be conducted at atmospheric pressure or at higher pressures, with moderate pressures up to about 300 psig being preferred. A most useful pressure range is from about 50 psig to about 200 psig. To insure that the amount of oxygen reacting with the phenol does not exceed that stoichiometrically required, the amount of oxygen in contact with the phenol can be, in general, controlled by limiting the flow of gas through or into the reaction vessel. Alternatively, it is sometimes advantageous to introduce amounts of an oxygen containing gas greater than that stoichiometrically required for the amount of phenol present, and to limit the amount of oxygen which actually reacts with the phenol by controlling the contact time between reactants and/or choice of type and concentration of catalyst and reaction temperature.

The reaction can be conducted at a temperature from about 50° C. to about 240° C., and preferably at a temperature that ranges from the melting temperature of the reaction mixture (generally about 175° C. to 180° C.) to about 200° C.

The process should be carried out for the time sufficient to convert substantially all of the phenol reactant to the corresponding biphenol. The length of time for optimum yield will depend upon the reaction temperature, type and amount of catalyst and induction period for the reaction. In general, excellent yields of substituted biphenol are obtained in from about 30 minutes to about one hour. Conversion of substituted phenols to the corresponding biphenols in accordance with the practice of the invention will result in substantially no by-product formation, including the formation of substantially no diphenoquinones.

Dealkylation of the substituted biphenols to prepare p,p'-biphenol may then be carried out using any of the dealkylating techniques known in the art. For the dealkylation reaction, it is not necessary to first recover the substituted biphenol, though, if desired, the biphenol can be readily recovered from the reaction mixture with generally only the separation of unreacted phenols and some water from the biphenol being necessary.

In a preferred embodiment, the dealkylation process conditions of the present invention are employed to prepare the desired p,p'-biphenol. In such event, the dealkylation reaction is carried out using the process steps and conditions in accordance with the practice of the invention hereinabove described.

Upon completion of the oxidative dimerization reaction, the substituted biphenol reaction product is heated to the desired dealkylation temperature in the absence of a catalyst while maintaining an inert, non-reactive atmosphere within the reaction vessel. Removal of olefin by-products from the reaction vessel may be carried out intermittently or continuously, as desired. The dealkylation reaction is carried out until substantially all of the substituted biphenol is converted to p,p'-biphenol and the p,p'-biphenol is then recovered from said reaction mixture using techniques hereinabove described.

If desired, the process of the invention may alternatively be conducted to continuously produce substituted biphenols in high yields with the substituted phenols formed thereby being dealkylated to p,p'-biphenol either by batch or continuous dealkylation procedures.

The invention will become more clear when considered together with the following examples which are set forth as being merely illustrative of the invention and which are not intended, in any manner, to be limitative thereof. Unless otherwise indicated, all parts and percentages are by weight.

EXAMPLE 1

A laboratory reactor is charged at 25° C. with 300 parts of solid 4,4'-bis (2,6-di-tert-butyl phenol) and heated to 330° C. at atmospheric pressure under a nitrogen blanket. The color of the starting dimer was dark green. The solid dimer melts down at approximately 185° C., and mild agitation is then applied to the dealkylation mixture, sufficient to maintain a uniform temperature profile in the reactor. The dealkylation commenced at approximately 300° C. as evidenced by the evolution of isobutylene gas from the reactor. As the thermal dealkylation proceeded, the reactor temperature was raised to and held at 330° C. for approximately 3½ hours. Gas chromatography analysis of the crude reaction product showed a conversion of 4,4'-bis (2,6-di-tert-butyl phenol) to p,p'-biphenol of 97%. Substantially no impurities were found (less than 1.5%) and the color of the crude p,p'-biphenol was dark brown.

The crude product was then sublimed out of the reactor by reducing the pressure to 6 mm-Hg and holding the temperature at approximately 300° C. Purified p,p'-biphenol was then precipitated out of the vapor phase by cooling the gas to about 50° C. and collecting the purified product in a separate receiver. 125 parts of purified p,p'-biphenol were recovered, thus the overall process efficiency was approximately 92%. Analysis of the purified p,p'-biphenol by gas chromatography showed 99.4% purity. The color of the final product was snow white. The color of the purified p,p'-biphenol was further evaluated by measuring the absorbance of a 10% solution of purified p,p'-biphenol in tetrahydrofuran, at 425 nm on a Fisher Electrophotometer II. An absorbance of only 0.20 was measured in a 1 cm cell, which showed the excellent color properties of this p,p'-biphenol.

EXAMPLE 2

4044 Grams of crude 2,6-di-tert-butyl phenol dimer were charged to an electrically heated stainless steel reactor. The reaction temperature was first raised to approximately 280° C. for 2 hours, maintaining a nitrogen blanket on the system. During this time, 1200 grams of volatiles, mostly unreacted 2,6-di-tert-butyl phenol and some mono-2-tert-butyl phenol, was distilled off. The reactor temperature was then raised to 300° C. for 4 hours and the isobutylene by-product was vented. The residue, mostly crude p,p'-biphenol of dark brown color, was distilled through a short fractionation column at a temperature of 320° C. and a pressure of only 150 mm-Hg. 1155 Grams of purified p,p'-biphenol were collected in a separate receiver, thus the overall process efficiency was about 90%. The color of the distilled p,p'-biphenol was snow white.

EXAMPLE 3

This example illustrates the preparation of high purity p,p'-biphenol starting with the oxidative coupling reaction of 2,6-di-tert-butyl phenol to prepare the corresponding biphenol followed by thermal dealkylation of the biphenol to p,p'-biphenol and product recovery by distillation.

A mixture of 200 grams (0.968 moles) of 2,6-di-tert-butyl phenol and 2 grams of a 50 percent aqueous potassium hydroxide solution was prepared in an autoclave reactor vessel having magnetically driven agitation means and temperature controlling means. The vessel was closed and brought to a temperature of about 180° C. Pure oxygen was admitted to a 100 psig internal pressure while agitation (about 460 rpm) was imparted to the reaction mixture. Initially, a mild exotherm took place (temperature increased to about 200° C.) along with a rapid oxygen pressure drop (to 75 psig). The pressure was brought back to 100 psig by adding oxygen several times within a 35 minute reaction time.

After 35 minutes reaction time, the reactor was purged with nitrogen and the contents were analyzed by gas chromatography: approximately 75% of the substituted phenol had been converted to the corresponding dimer. The material temperature was then raised to 300° C., and the unreacted 2,6-di-tert-butyl phenol was distilled out of the reactor. As the dealkylation proceeded, the temperature was raised to 320° C. and the isobutylene by-product was vented. After 4 hours reaction time, the crude p,p'-biphenol was distilled under vacuum using the procedure of Example 2. The distilled p,p'-biphenol had a snow white color and was of excellent quality.

It can be seen from this example that it is not necessary to recover the 2,6-di-tert-butyl phenol dimer from the reaction product of the oxidative dimerization reaction prior to thermal dealkylation thereof to thermal dealkylation thereof to prepare p,p'-biphenol.

EXAMPLE 4

This example illustrates that purified p,p'-biphenol as obtained in Example 1, is a polymer grade monomer. The preparation of a polyphenylsulfone condensation polymer is carried out using the following proportions of materials:

| | |
|---|---|
| p,p'-biphenol (Example 1) | 37.43 g (0.20 mole) |
| Dichlorodiphenyl sulfone | 57.44 g (0.20 mole) |
| Potassium carbonate | 41.46 g (0.30 mole) |
| Dimethylacetamide (DMAC) | 170 ml |
| Toluene | 70 ml |

A 250 ml 3-neck flask equipped with an overhead mechanical stirrer, a nitrogen inlet tube, thermometer, Dean-Stark trap and reflux condenser is charged with dichlorodiphenyl sulfone, $K_2CO_3$ (anhyd. powder), toluene and DMAC.

The reaction mixture is sparged with nitrogen at room temperature, p,p'-biphenol is added and the nitrogen sparge is continued for an additional 10 minutes. The reaction temperature is raised to 136° C. at which point a water/toluene azeotrope is collected in a Dean-Stark trap.

The temperature is further increased to 160° C., removing water continuously by the toluene azeotrope. After 6 hours (total heating time), the polymer begins wrapping around the paddle stirrer. The reaction mixture is diluted with DMAC and the polymer is terminated with methyl chloride which is bubbled into the solution for 15 minutes at 130° C. The polymer is filtered at 100° C. to remove the potassium salts and the filtrate acidified with oxalic acid. The resulting solution at 80° C. is coagulated from water (5:1 water to polymer solution), filtered, slurried in hot water for 1 hour, refiltered and again washed with methanol. The wet polymer is dried overnight under vacuum at 100° C. The resulting polymer has a reduced viscosity of 0.69 (measured at 25° C. at a concentration of 0.2 g/100 ml of N-Methyl-Pyrrolidone). A compression molded sample of the same polymer showed a pendulum impact of 190 ft-lb/in$^3$, tensile strength of 10,000 psi, a modulus of 290,000 psi, and a glass transition temperature of 216° C. These excellent mechanical and physical properties obtained in the polymer sample prepared with the p,p'-biphenol of example 1 clearly shows its suitability and quality as a polymer grade monomer.

What is claimed is:

1. A process for producing p,p'-biphenol which comprises heating a 4,4'-bis(substituted phenol) at elevated temperatures below the decomposition temperature of p,p'-biphenol in the absence of a catalyst under an inert non-reactive atmosphere for the length of time sufficient to obtain a reaction product containing a substantial amount of p,p'-biphenol while removing the olefin by-product formed and then recovering the p,p'-biphenol product.

2. The process of claim 1 wherein the olefin by-product is continuously removed from the dealkylation reaction as it is formed.

3. The process of claim 1 wherein said 4,4'-bis (substituted phenol) is heated at a temperature between about 250° C. and about 500° C.

4. The process of claim 1 wherein said p,p'-biphenol product is revovered by an evaporation and condensation procedure.

5. A process for producing p,p'-biphenol which comprises:

(a) contacting a phenol having the formula

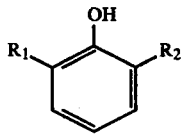

wherein $R_1$ and $R_2$ may be the same or different and is a member selected from the group consisting of alkyl radicals containing from 2 to 10 carbon atoms, aralkyl radicals containing from 8 to 10 carbon atoms and having a β alkyl carbon—hydrogen group, and cyclic alkyl radicals having a β alkyl carbon—hydrogen group with oxygen or an oxygen containing gas in the presence of a catalytic quantity of a catalyst selected from the group consisting of alkali metal hydroxides, alkali metal salts of a weak acid, alkaline earth metal hydroxides, alkaline earth metal salts of a weak acid, amine bases, and mixtures of the same at an elevated temperature for the time necessary to react up to a stoichiometric amount of oxygen with said phenol to form a reaction product containing a substantial amount of 4,4'-bis(2,6-disubstitutedphenol);

(b) dealkylating the substituent groups other than hydroxyl from said biphenol, said dealkylating comprises heating said biphenol reaction product at an elevated temperature below the decomposition temperature of p,p'-biphenol in the absence of a catalyst under an inert, non-reactive atmosphere for the length of time sufficient to obtain a reaction product containing a substantial amount of p,p'-biphenol while removing the olefin by-product formed, and then (c) recovering said p,p'-biphenol.

* * * * *